United States Patent [19]  [11] 4,221,817
Tenne  [45] Sep. 9, 1980

[54] METHOD FOR THE CONTROL OF PHYTOPATHOGENIC FUNGI USING PHENYLALKOXYPHENYLUREA COMPOUNDS

[75] Inventor: Frank D. Tenne, Plainsboro, N.J.

[73] Assignee: American Cyanamid Company, Stamford, Conn.

[21] Appl. No.: 30,679

[22] Filed: Apr. 16, 1979

[51] Int. Cl.² ............................................. A01N 9/12
[52] U.S. Cl. ..................................... 424/322; 71/120; 260/553 A
[58] Field of Search .................... 424/322; 260/553 A

[56] References Cited

U.S. PATENT DOCUMENTS 3,951,641  4/1976  Janiak .............................. 260/553 A
4,129,436  12/1978  Tahemoto et al. .................... 71/120

Primary Examiner—Allen J. Robinson
Attorney, Agent, or Firm—Harry H. Kline

[57] ABSTRACT

There is provided a method for the control of phytopathogenic fungi either by contacting the same with a phenylalkoxyphenylurea compound, or by applying said urea to the foliage of a plant susceptible to attack by fungi.

13 Claims, No Drawings

METHOD FOR THE CONTROL OF PHYTOPATHOGENIC FUNGI USING PHENYLALKOXYPHENYLUREA COMPOUNDS

SUMMARY OF THE INVENTION

The present invention relates to a method for the control of phytopathogenic fungi with a fungicidally effective amount of a compound of formula (I):

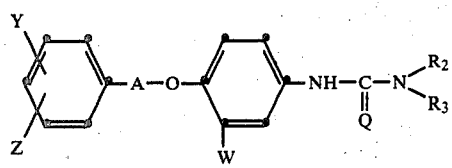

wherein Q is O or S; Y is selected from the group consisting of hydrogen, Cl, $CH_3$, $CH_3O$, F and $NO_2$; Z is hydrogen or $CH_3O$; W is selected from the group consisting of hydrogen, $CH_3$, $CH_3O$, Cl and $NO_2$; $R_2$ is hydrogen, $CH_3$ and $C_2H_5$; $R_3$ is $CH_3$ and $C_2H_5$; A is a $C_2$-$C_8$ carbon chain (straight or branched) which may be saturated or unsaturated.

A preferred group of compounds of formula (I) are those wherein A is selected from

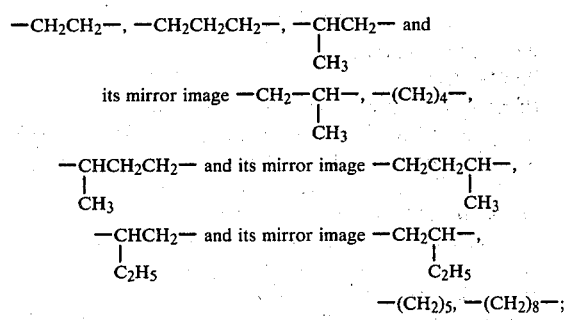

is selected from hydrogen, F, Cl, $CH_3$ and $OCH_3$; and Q, Y, Z, W, $R_2$ and $R_3$ are as hereinabove defined.

A more preferred group of compounds of formula (I) are those wherein Z is hydrogen; $R_2$ is hydrogen or $CH_3$; and $R_3$ is $CH_3$; W is $CH_3$, $CH_3O$ and Cl; A is selected from

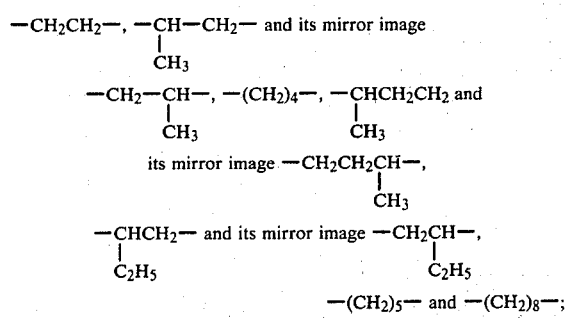

Q is as hereinabove defined; and Y is selected from hydrogen, F, Cl and $CH_3$.

The fungicidal compounds of formula (I), wherein X is O, and A is $C_2$-$C_8$ alkylene, may be conveniently prepared by the route shown below:

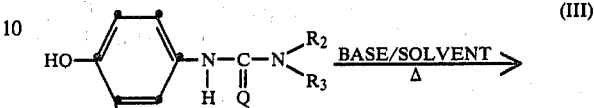

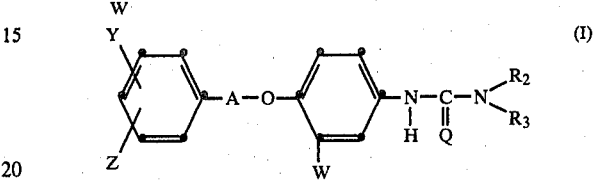

wherein Q, Y, Z, W, $R_2$ and $R_3$ are as hereinabove defined; and L is selected from $-OSO_2CH_3$ or halide. Thus, the methanesulfonate ester of the appropriately substituted phenylalkanol, or the corresponding phenalkylhalide of formula (II), is reacted with a ureidophenol of formula (III) in the presence of an inorganic or organic base, preferably potassium t-butoxide, and a solvent, such as dimethylformamide, in the temperature range of from about 20° C. to about 90° C., and preferably 60° C. to 80° C., for a period of time sufficient to essentially complete the reaction.

An alternate route leading to formula (I) compounds comprises reacting an isocyanate or isothiocyanate of formula (X):

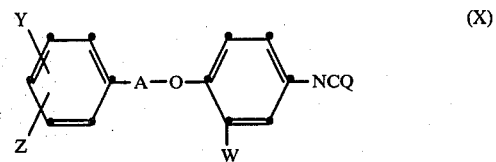

with an equimolar or excess amount of an amine of formula

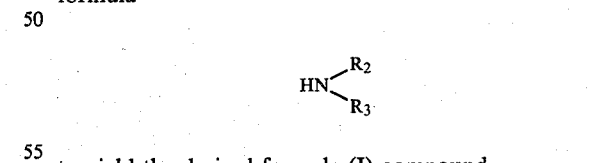

to yield the desired formula (I) compound:

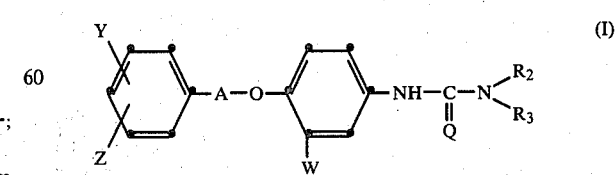

wherein Y, Z, W, Q, $R_2$ and $R_3$ are as hereinabove defined.

Similarly, the appropriate aniline of formula (XI):

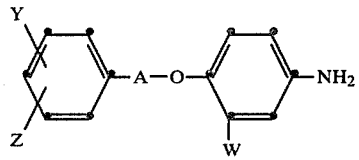

may be reacted with an isocyanate of formula: R$_3$—NCO to yield a formula (I) compound of structure:

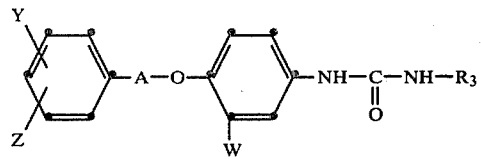

The compounds of the present invention, as hereinabove defined, find utility as a control of fungi which infect living plants. They are especially useful and effective for the control of fungi which are the causative agents for rice blast and apple scab. They are also useful for the control of powdery mildew on grains, such as wheat or barley, on vines, such as grapes, and in fruit and nut trees, such as apples, pears and pecans.

To protect plants from pathogenic fungi, theureas of the present invention are applied to the foliage of the plant in the form of a liquid, preferably aqueous, spray. Solutions or suspensions containing from about 20 ppm to about 1000 ppm, and preferably 50 ppm to 500 ppm, of formula (I) urea are generally highly effective for this use.

The compounds of the invention can be formulated as emulsion concentrates, flowable concentrates, or wettable powders which are diluted with water or another suitable polar solvent, generally in situ, and then applied as a dilute spray.

Usually, such sprays are applied at a rate of from about 700 l/ha to about 1900 l/ha. Obviously, smaller or larger volumes of liquid spray may be employed, depending on a plurality of factors, such as type of crop, the plant spacing, and the amount of foliage being treated.

Wettable powders can be prepared by grinding and blending together about 25% to 85% by weight of formula (I) urea and about 75% to 15% by weight of a solid diluent, such as bentonite, diatomaceous earth, kaolin, attapulgite, and the like. To this mixture is added about 1% to 5% by weight of a dispersing agent, such as the calcium salt of a polymerized alkyl aryl sulfonic acid, sodium lignosulfonate, or the sodium salt of condensed naphthalene sulfonic acid, and about 1% to 5% by weight of a surfactant, such as polyoxyethylated vegetable oil, alkyl phenoxy polyoxyethylene ethanol, sodium alkyl sulfonate, alkyl polyoxyethylene ethers, polyoxyethylene (20) sorbitan monolaurate and monooleate, and the like, is also blended with the formulation.

Emulsion concentrates are prepared by dissolving 15% to 70% by weight of the compound in 85% to 30% by weight of a solvent, such as benzene, toluene, xylene, kerosene, 2-methoxyethanol, propylene glycol, diethylene glycol, diethylene glycol monomethyl ether, formamide, methylformamide, and the like, and mixtures thereof. Advantageously, surfactants, such as polyoxyethylated vegetable oil, or an alkyl phenoxy polyoxyethylene ethanol, are also incorporated in amounts of 1% to 5% by weight of said concentrate.

Application of the material is made by adding a predetermined quantity of formulated product, such as described above, to the desired volume of water or other suitable solvent, alone or in combination with other agronomic chemicals for simultaneous use.

In addition to being valuable fungicides, the compounds of the present invention, represented and described by formula (I) above, are valuable herbicides.

The invention is further illustrated by the examples set forth below, which are provided by way of illustration and not by way of limitation.

EXAMPLE 1

Evaluation of the Fungicidal Activity of Compounds of the Invention

To determine the effectiveness of the phenyl alkoxyphenylurea compounds as fungicidal agents, a variety of pathogenic fungi, host plants, and urea compounds are used in the following tests. Pathogen, host plants, the method of testing, and the rating system used are reported below, along with the data obtained.

Pathogens

RB = Rice Blast [*Piricularia oryzae* (Carv.)]
AS = Apple Scab [*Venturia inaequalis* (Cke.) Wint.]

Host Plants

Rice (*Oryza sativa*)
Apple (*Malus sylvestris*)

Plants are individually grown in 5 cm peat squares and assembled in fiber flats prior to spraying. Several plants/peat square of rice, and a single seedling of apple is used. Spray solution are prepared in the final concentrations in the appropriate volume of 50% aqueous acetone. Spray to runoff is provided by two Spray System Company nozzles mounted to deliver vertical and horizontal solid cone patterns. Test plants are returned to the greenhouse immediately after application of test solutions and allowed to dry.

Plants are inoculated with aqueous spore suspensions of the respective pathogens using a DeVilbiss Atomizer and transferred to a controlled temperature/humidity cabinet (21° C., RH 95%) for 3 days. Plants are then removed from the cabinet and transferred to the greenhouse to await disease development. Ratings are taken for disease severity on a scale of 1–7, as described below.

| Disease Rating | Disease Percentage | |
|---|---|---|
| | Range | Midpoint |
| 1 | 0 | 0 |
| 2 | 0–8.4 | 4.2 |
| 3 | 8.5–21.4 | 14.9 |
| 4 | 21.5–78.6 | 50.0 |
| 5 | 78.7–91.6 | 85.1 |
| 6 | 91.7–99.9 | 95.8 |
| 7 | 100 | 100 |

Disease severity scores are converted to estimated percentages from tables adjusted to the 1–7 scale based on those published by Elanco for the 12-point Barrett-Horsefall rating scale. Disease percentages are then converted to percent disease control according to the following formula:

$$\frac{\text{Disease Incidence Control}(\%) - \text{Disease Incidence Treatment}(\%)}{\text{Disease Incidence Control}(\%)} \times 100 = \text{Percent Disease Control.}$$

Phytotoxicity (if present) of the compounds of the invention is indicated by the use of the following symbols:

sl=slight injury
mod=moderate injury
sv=severe injury

The word, "phytotoxic," is used to indicate that all plants or treated leaves in all replicates are killed by the compound and no rating could be taken.

Data obtained are reported in Table I below.

TABLE I

Evaluation of Phenylalkoxyphenyl Urea Compounds for the Control of Plant Pathogenic Fungi

| Compound | Rate ppm | Percent Control of RB | Percent Control of AS |
|---|---|---|---|
| 3-[3-Chloro-4-(cinnamyloxy)phenyl]-1,1-dimethylurea | 500 | | 95 |
| | 100 | | 94 sv |
| | 50 | | |
| 3-[3-Chloro-4-(5-phenylpentyloxy)phenyl]-1,1-dimethylurea | 500 | 95 | |
| | 100 | 99 | |
| | 50 | 94 | |
| 3-[3-Chloro-4-(phenethyloxy)phenyl]-1,1-dimethylurea | 500 | 100 | 100 sv |
| | 100 | 98 | phytotoxic |
| | 50 | 100 | 97 sv |
| 3-[3-Chloro-4-(4-phenylbutoxy)phenyl]-1,1-dimethylurea | 500 | 95 | phytotoxic |
| | 100 | 100 | 96 sl |
| | 50 | 98 | 85 sl |
| 3-[3-Chloro-4-(4-fluorophenethyloxy)phenyl]-1,1-dimethylurea | 500 | 95 | phytotoxic |
| | 100 | 93 | 97 mod |
| | 50 | 88 | 99 mod |
| 3-[3-Chloro-4-(β-methylphenethyloxy)phenyl]-1,1-dimethylurea | 500 | phytotoxic | 100 sv |
| | 100 | 97 | 100 sv |
| | 50 | 97 | 95 mod |
| 3-[3-Chloro-4-(α-methylphenethyloxy)phenyl]-1,1-dimethylurea | 500 | 95 | |
| | 100 | 96 | |
| | 50 | 94 | |
| 1-[3-Chloro-4-(phenethyloxy)phenyl]-3-methylurea | 500 | * | |
| | 100 | 94 | |
| | 50 | 96 | |
| 1-[3-Chloro-4-(3-phenylpropoxy)phenyl]-3-methylurea | 500 | 92 | phytotoxic |
| | 100 | 93 | 94 mod |
| | 50 | 91 | 85 sl |
| 1,1-Dimethyl-3-[3-nitro-4-(3-phenylpropoxy)phenyl]urea | 500 | 95 | 85 mod |
| | 100 | 89 | |
| | 50 | IA | |
| 3-[3-Chloro-4-(phenethyloxy)phenyl]-1,1-diethylurea | 500 | 92 | |
| | 100 | | |
| | 50 | | |
| 3-[3-Chloro-4-(4-methylphenethyloxy)phenyl]-1,1-dimethylurea | 500 | 100 | 84 mod |
| | 100 | 97 | 84 mod |
| | 50 | 91 | |
| 1,1-Dimethyl-3-[3-nitro-4-(phenethyloxy)phenyl]urea | 500 | 95 | 84 |
| | 100 | 72 | |
| | 50 | 80 | |
| 3-[3-Chloro-4-(3-phenylbutoxy)phenyl]-1,1-dimethylurea | 500 | 93 | |
| | 100 | 94 | |
| | 50 | 96 | |
| 3-[3-Chloro-4-(8-phenyloctyloxy)phenyl]-1,1-dimethylurea | 500 | 93 | |
| | 100 | 89 | |
| | 50 | 92 | |
| 3-[3-Chloro-4-(1-methyl-3-phenylpropoxy)phenyl]-1,1-dimethylurea | 500 | 95 | |
| | 100 | 98 | |
| | 50 | 93 | |
| 3-[3-Chloro-4-(β-ethylphenethyloxy)phenyl]-1,1-dimethylurea | 500 | 95 | 96 mod |
| | 100 | 83 | 94 sl |
| | 50 | 77 | 94 mod |
| 3-[3-Chloro-4-(phenethyloxy)phenyl]-1,1-dimethylthiourea | 500 | 95 | |
| | 100 | 97 | |
| | 50 | 97 | |
| 3-{3-Chloro-4-[2-(2-naphthyl)ethoxy]phenyl}-1,1-dimethylurea | 500 | 95 | 96 mod |
| | 100 | 68 | 89 mod |
| | 50 | 91 | 89 mod |
| 3-[3-Chloro-4-(3,4-dimethoxyphenethoxy)phenyl]-1,1-dimethylurea | 500 | 95 | |

TABLE I-continued

Evaluation of Phenylalkoxyphenyl Urea Compounds for the Control of Plant Pathogenic Fungi

| Compound | Rate ppm | Percent Control of RB | Percent Control of AS |
|---|---|---|---|
| ethoxy)phenyl]-1,1-dimethylurea | 100 | 89 | |
| | 50 | 72 | |
| 1-[3-Chloro-4-(phenethyloxy)phenyl]-3-methylthiourea | 500 | 100 | |
| | 100 | 94 | |
| | 50 | 92 | |
| 1,1-Dimethyl-3-[4-(β-methylphenethyloxy)phenyl]urea | 500 | 91 | 100 sv |
| | 100 | | |
| | 50 | | |
| 3-[3-Chloro-4-(4-nitrophenethyloxy)phenyl]-1,1-dimethylurea | 500 | 91 | |
| | 100 | | |
| | 50 | | |
| 1,1-Dimethyl-3-[4-(3-phenyl-2-propynyloxy]urea | 500 | 91 | |
| | 100 | | |
| | 50 | | |
| 3-[3-Chloro-4-[α-ethylphenethyloxy)phenyl]-1,1-dimethylurea | 500 | 100 | 84 mod |
| | 100 | | |
| | 50 | | |
| 1-[3-Chloro-4-(α-methylphenethyloxy)phenyl]-3-methylurea | 500 | 91 | |
| | 100 | | |
| | 50 | | |
| 1-[3-Chloro-4-(β-methylphenethyloxy)phenyl]-3-methylurea | 500 | 100 | 96 |
| | 100 | | |
| | 50 | | |
| 1,1-Dimethyl-3-[3-methyl-4-(3-phenylpropoxy)phenyl]urea | 500 | 91 | 100 sv |
| | 100 | | |
| | 50 | | |
| 3-[3-Methoxy-4-(phenethyloxy)phenyl]-1,1-dimethylurea | 500 | 100 | 100 sv |
| | 100 | | |
| | 50 | | |
| 3-[3-Chloro-4-(4-chlorophenethyloxy)phenyl]-1,1-dimethylurea | 500 | * | |
| | 100 | 89 | |
| | 50 | | |
| 3-[4-(α-Ethylphenethyloxy)phenyl]-1,1-dimethylurea | 500 | 67 | 84 |
| | 100 | | |
| | 50 | | |

*No valid data available due to low disease incidence on control plants.

EXAMPLE 2

General Methods for the Preparation of Fungicidal Phenylalkoxyphenylurea Compounds

Method A

The appropriate ureidophenol (0.03 mol), dimethylformamide (DMF; 200 ml) and potassium t-butoxide (0.03 mol) are mixed and stirred at room temperature under a nitrogen atmosphere for one hour. Next, the appropriate methanesulfonate ester (0.03 mol) is added, and the reaction mixture heated at 80° C. from 2 to 18 hours. The solution is then cooled down, and the DMF removed under vacuum. The residue is dissolved in methylene chloride and water (made basic with a few drops of 1 N sodium hydroxide). The organic layer is washed with water and filtered through a 5 cm thick layer of neutral alumina. The alumina layer is washed with acetonitrile, filtrate and washings are combined and evaporated to afford the desired urea. The product may be further purified by recrystallization from a suitable solvent.

Method B

The appropriate dialkylamine (2 to 4 moles) is added to a solution of the appropriately substituted phenylisocyanate (1 mol) in toluene under a nitrogen atmosphere. The reaction mixture exotherms and then cools to ambient temperature. The reaction mixture is stirred overnight and then treated with 10% aqueous sodium hydroxide. The organic layer is then separated, washed in succession with 10% aqueous sodium hydroxide, water, dilute hydrochloric acid, water and brine. The solution is dried over potassium carbonate, and concentrated under vacuum to yield the desired urea. The product may be further purified by recrystallization from a suitable solvent.

Method C

The appropriate alkylisocyanate (1.2–1.3 mol) is added to a solution of the appropriately substituted aniline (1 mol) in toluene under a nitrogen atmosphere. The reaction mixture is stirred at room temperature for about 16–24 hours, and the product is isolated by standard laboratory procedures from the reaction mixture.

The compounds of the present invention are made by one or more of the above methods and are summarized in Table II below.

TABLE II

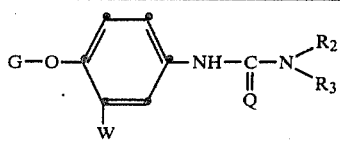

| G | W | Q | $R_2$ | $R_3$ | Melting Point °C. |
|---|---|---|---|---|---|
| ⌬—CH=CH—CH2 | Cl | O | CH3 | CH3 | 157.5–158.5 |
| ⌬—(CH2)5 | Cl | O | CH3 | CH3 | 83–84 |
| ⌬—CH2CH2 | Cl | O | CH3 | CH3 | 113–114 |
| ⌬—(CH2)4 | Cl | O | CH3 | CH3 | 79–81 |
| F—⌬—CH2CH2 | Cl | O | CH3 | CH3 | 111–112 |
| ⌬—CHCH2 / CH3 | Cl | O | CH3 | CH3 | 94.5–96.5 |
| ⌬—CH2CH / CH3 | Cl | O | CH3 | CH3 | 101–104 |
| ⌬—CH2CH2 | Cl | O | H | CH3 | 136–136.5 |
| ⌬—CH2CH2CH2 | Cl | O | H | CH3 | 105–106.5 |

TABLE II-continued

| G | W | Q | $R_2$ | $R_3$ | Melting Point °C. |
|---|---|---|---|---|---|
| ⌬—CH2CH2 | Cl | O | C2H5 | C2H5 | 89–90 |
| CH3—⌬—CH2CH2 | Cl | O | CH3 | CH3 | 110–111 |
| ⌬—CH2CH2 (NO2) | NO2 | O | CH3 | CH3 | 90–92 |
| ⌬—CHCH2CH2 / CH3 | Cl | O | CH3 | CH3 | 101.5–102 |
| ⌬—(CH2)8 | Cl | O | CH3 | CH3 | 59–59.5 |
| ⌬—CH2CH2CH / CH3 | Cl | O | CH3 | CH3 | 70–72(d) |
| ⌬—CHCH2 / C2H5 | Cl | O | CH3 | CH3 | 105–106 |
| ⌬—CH2CH2 | Cl | S | CH3 | CH3 | 110–111 |
| naphthyl—CH2CH2 | Cl | O | CH3 | CH3 | 130.5–132.5 |
| CH3O—⌬(CH3O)—CH2CH2 | Cl | O | CH3 | CH3 | 114–117 |
| ⌬—CH2CH2 | Cl | S | H | CH3 | 124–125 |

EXAMPLE 3

General Procedure for the Preparation of Esters of Methanesulfonic Acid

A solution of the appropriate alcohol (0.1 mol) and triethylamine (0.15 mol) in methylene chloride (150 ml) is rapidly stirred, chilled to −15° C., and methanesulfonyl chloride (0.11 mol) added at a rate to maintain the reaction temperature below −10° C. After the addition is completed, the solution is stirred for 30 minutes in the cold, and then at room temperature for 2 hours. Next, the methylene chloride solution is separated, washed with ice-cold water, ice-cold 10% hydrochloric acid, saturated sodium bicarbonate solution, saturated brine, and then dried over sodium sulfate. Finally, the appropriate ester is isolated by evaporating the methylene chloride solution under vacuum.

Esters of methanesulfonic acid prepared by the above procedure are listed in Table III below, together with their physical data, when such is available.

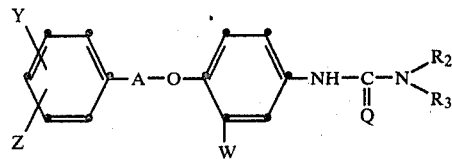

wherein Q is O or S; Y is selected from the group consisting of hydrogen, Cl, $CH_3$, $CH_3O$, F and $NO_2$; Z is hydrogen or $CH_3O$; W is selected from the group con-

TABLE III

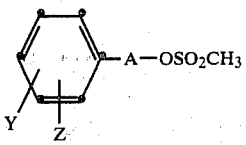
$A-OSO_2CH_3$

| No. | Y | Z | A | Melting Point °C. | Analysis Calculated | Found | Remarks |
|---|---|---|---|---|---|---|---|
| 1 | p-$CH_3$ | H | $CH_2-CH_2$ | 50-52 | C, 56.05 | 55.80 | |
| | | | | | H, 6.58 | 6.71 | |
| | | | | | S, 14.96 | 14.71 | |
| 2 | H | H | $CH_3$<br>\|<br>$CH_2-CH-$ | straw oil | C, 56.05<br>H, 6.58<br>S, 14.96 | 56.12<br>6.76<br>15.18 | |
| 3 | H | H | $(CH_2)_4-$ | straw oil | C, 57.87<br>H, 7.07<br>S, 14.05 | 58.70<br>7.36<br>13.75 | |
| 4 | p-F | H | $CH_2-CH_2$ | brown oil | C, 49.53<br>H, 5.08<br>S, 8.73<br>F, 14.69 | 49.82<br>5.04<br>8.60<br>14.69 | |
| 5 | H | H | $CH_3$<br>\|<br>$CH-CH_2$ | amber oil | | | Lit. J.O.C. 38(8) 1518 (1973) |
| 6 | H | H | $(CH_2)_3$ | amber oil | C, 56.04<br>H, 6.54<br>S, 14.96 | 55.98<br>6.71<br>14.94 | |
| 7 | H | H | $(CH_2)_5$ | amber oil | C, 54.48<br>H, 7.49<br>S, 13.23 | 54.72<br>7.86<br>13.08 | |
| 8 | H | H | $CH_2-CH_2$ | amber oil | | | Lit. J.O.C. 38(8) 1518 (1973) |
| 9 | H | H | $CH_3$<br>\|<br>$CH_2CH_2CH$ | straw oil | C, 57.87<br>H, 7.07<br>S, 14.05 | 57.23<br>7.14<br>12.96 | |
| 10 | H | H | $C_2H_5$<br>\|<br>$CH-CH_2$ | brown oil | C, 57.87<br>H, 7.07<br>S, 14.05 | 57.91<br>7.19<br>13.97 | |
| 11 | p-$NO_2$ | H | $CH_2-CH_2$ | 80.5-82.5 | | | J.O.C. 38(8) 1518 (1973) Lit. 80-81° C. |
| 12 | p-$OCH_3$ | m-$OCH_3$ | $CH_2-CH_2$ | yellow oil | C, 50.75<br>H, 6.20<br>S, 12.32 | 50.42<br>5.74<br>12.23 | |
| 13 | H | H | $C_2H_5$<br>\|<br>$CH_2-CH$ | brown oil | C, 57.87<br>H, 7.07<br>S, 14.05 | 58.03<br>7.21<br>13.86 | |
| 14 | H | H | $CH_3$<br>\|<br>$CH-CH_2-CH_2$ | | C, 58.87<br>H, 7.07<br>S, 14.05 | 58.17<br>7.38<br>13.88 | |

We claim:

1. A method for the control of fungi comprising, contacting said fungi causing rice blast, apple scab and powdery mildew with a fungicidally effective amount of a compound having the formula:

sisting of hydrogen, $CH_3$, $CH_3O$, Cl and $NO_2$; $R_2$ is hydrogen, $CH_3$ and $C_2H_5$; $R_3$ is $CH_3$ and $C_2H_5$; A is a $C_2-C_8$ carbon chain (straight or branched) which may be saturated or unsaturated.

2. A method according to claim 1, wherein A is selected from $-CH_2CH_2-$, $-CH_2CH_2CH_2-$, $-CHCH_2-$ and
                                          $\quad\quad\quad\quad\quad\quad\quad\quad\quad$ |
                                          $\quad\quad\quad\quad\quad\quad\quad\quad\quad CH_3$ -continued its mirror image —CH$_2$CH—, —(CH$_2$)$_4$—,
                    |
                    CH$_3$ —CHCH$_2$CH$_2$— and its mirror image —CH$_2$CH$_2$CH—,
   |                                        |
   CH$_3$                                    CH$_3$ —CHCH$_2$— and its mirror image —CH$_2$CH—,
   |                               |
   C$_2$H$_5$                       C$_2$H$_5$

—(CH$_2$)$_5$—, —(CH$_2$)$_8$—,

Y is selected from hydrogen, F, Cl, CH$_3$ and OCH$_3$; and Q, Z, W, R$_2$ and R$_3$ are as defined in claim 1.

3. A method according to claim 1, wherein Z is hydrogen, R$_2$ and R$_3$ each are CH$_3$ or C$_2$H$_5$; W is CH$_3$, CH$_3$O and Cl; A is selected from —CH$_2$CH$_2$—, —CH—CH$_2$—and
                |
                CH$_3$ its mirror image —CH$_2$—CH—,
                         |
                         CH$_3$ —CHCH$_2$CH$_2$— and its mirror image —CH$_2$CH$_2$CH—,
   |                                        |
   CH$_3$                                    CH$_3$ —CHCH$_2$— and its mirror image —CH$_2$CH—, —(CH$_2$)$_5$—;
   |                               |
   C$_2$H$_5$                       C$_2$H$_5$ Y is selected from hydrogen, F, Cl and CH$_3$; and Q is as defined in claim 1.

4. A method according to claim 1, wherein said compound is 3-[3-chloro-4-(β-methylphenethyloxy)-phenyl]-1,1-dimethylurea.

5. A method according to claim 1, wherein said compound is 1-[3-chloro-4-(3-phenylpropoxy)phenyl]-3-methylurea.

6. A method according to claim 1, wherein said compound is 3-[3-chloro-4-(phenylbutoxy)phenyl]-1,1-dimethylurea.

7. A method according to claim 1, wherein said compound is 3-[3-chloro-4-(phenethyloxy)phenyl]-1,1-dimethylthiourea.

8. A method according to claim 1, wherein said compound is 3-[3-chloro-4-(phenyloxtyxy)phenyl]-1,1-dimethylurea.

9. A method to protect living plants from attack by fungi causing rice blast, apple scab and powdery mildew comprising, applying to the foliage of said plants a fungicidally effective amount of a compound represented by formula:

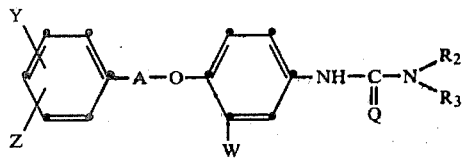

wherein Q is O or S; Y is selected from the group consisting of hydrogen, Cl, CH$_3$, CH$_3$O, F and NO$_2$; Z is hydrogen or CH$_3$O; W is selected from the group consisting of hydrogen, CH$_3$, CH$_3$O, Cl and NO$_2$; R$_2$ is hydrogen, CH$_3$ and C$_2$H$_5$; R$_3$ is CH$_3$ and C$_2$H$_5$; A is a C$_2$-C$_8$ carbon chain (straight or branched) which may be saturated or unsaturated.

10. A method according to claim 9, wherein A is selected from

—CH$_2$CH$_2$—, —CH$_2$CH$_2$CH$_2$—, —CHCH$_2$—and
                                        |
                                        CH$_3$ its mirror image —CH$_2$CH—, —(CH$_2$)$_4$—,
                    |
                    CH$_3$ —CHCH$_2$CH$_2$— and its mirror image —CH$_2$CH$_2$CH—,
   |                                        |
   CH$_3$                                    CH$_3$ —CH—CH$_2$—, —(CH$_2$)$_5$— and —(CH$_2$)$_8$—.
   |
   C$_2$H$_5$ 11. A method according to claim 9, wherein said plants are rice.

12. A method according to claim 9, wherein Q is S.

13. A method according to claim 9, wherein Q is O.

* * * * *